United States Patent [19]
Fujimoto

[11] Patent Number: 6,093,148
[45] Date of Patent: Jul. 25, 2000

[54] ULTRASONIC WAVE DIAGNOSIS APPARATUS

[75] Inventor: Katsuhiko Fujimoto, Urawa, Japan

[73] Assignee: Kabushiki Kaisha Toshiba, Kawasaki, Japan

[21] Appl. No.: 09/050,001

[22] Filed: Mar. 30, 1998

[30] Foreign Application Priority Data

Mar. 31, 1997 [JP] Japan .................................. 9-079867
Mar. 11, 1998 [JP] Japan ................................. 10-059556

[51] Int. Cl.[7] ........................................................ A61B 8/00
[52] U.S. Cl. ........................................... 600/439; 600/438
[58] Field of Search ............................... 600/439; 601/2, 601/3, 4

[56] References Cited

U.S. PATENT DOCUMENTS

| | | | |
|---|---|---|---|
| 5,080,102 | 1/1992 | Dory | 128/660.03 |
| 5,144,953 | 9/1992 | Wurster et al. | 600/439 |
| 5,150,712 | 9/1992 | Dory | 128/660.03 |
| 5,152,289 | 10/1992 | Viebach et al. | 600/439 |
| 5,553,618 | 9/1996 | Suzuki et al. | 128/653.1 |

*Primary Examiner*—Marvin M. Lateef
*Assistant Examiner*—Maulin Patel
*Attorney, Agent, or Firm*—Foley & Lardner

[57] ABSTRACT

When an affected region is greater than a focal point of a therapy ultrasonic wave, a therapy region is set in a way to include the affected region. The focal point of the therapy ultrasonic wave is moved along a planned course designed based on the therapy region, so that it is possible to treat that whole affected region greater than the focal point. In the present invention, before an actual therapy, that is, before irradiation with the therapy ultrasonic wave, a therapy simulation is made to see whether or not a better treatment is carried out. In the therapy simulation, an applicator is moved in accordance with a planned course designed based on the therapy region. During the movement, the internal region of a human subject is continuously scanned and imaged by the ultrasonic probe. A cross-sectional image obtained is displayed together with a focal point marker representing the focal point. In this way, the applicator is moved along an actual planned course and, by observing a positional relation between the subject and the focal point, accurate checking is made to see whether or not the therapy region is set relative to the affected region.

19 Claims, 5 Drawing Sheets

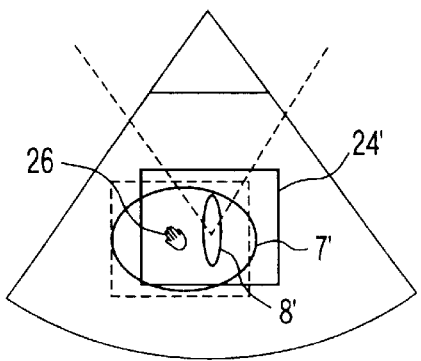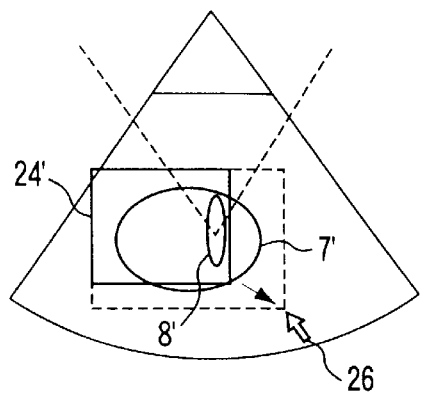
① ADJUSTING A POSITION OF THE CAUTERIZATION REGION (DRAGGING A MARK OF THE CAUTERIZATION REGION)
② ADJUSTING A SIZE OF THE CAUTERIZATION REGION
F I G. 5A
F I G. 5B
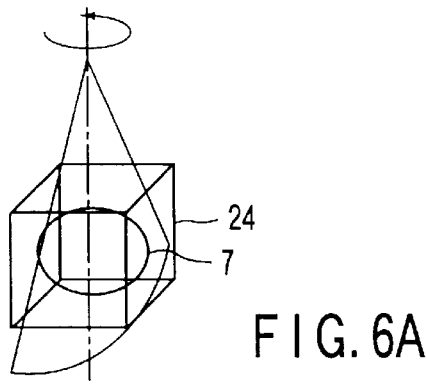
F I G. 6A
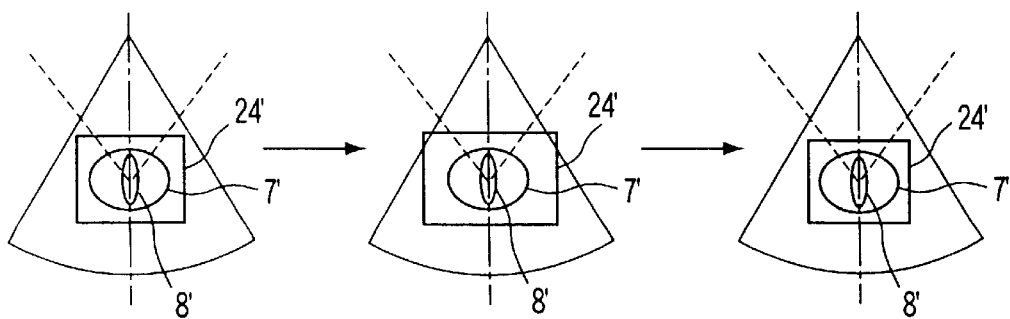
F I G. 6B

ULTRASONIC WAVE DIAGNOSIS APPARATUS

BACKGROUND OF THE INVENTION

The present invention relates to an ultrasonic wave diagnosis apparatus for enabling calculi present in a living body to be crushed by an ultrasonic wave and tumors, such as the cancers, to be cauterized.

In recent years, the trend now receiving attention in a medical field of treatment has been toward the treatment called an MIT (Minimally Invasive Treatment).

As one example, a calculus crushing apparatus has been practically realized whereby the calculus is invasively treated/crushed by irradiating a powerful ultrasonic wave from an external source at a calculus site in the living body. This has greatly changed the aspect of medical treatment on the calculi at the urinary organs. As such a powerful ultrasonic wave generating source there are known an underwater discharge, an electromagnetic induction, a microbursting, a piezoelectric, etc., system. Of these, the piezoelectric system in particular, though being smaller in its ultrasonic pressure in terms of its power, has various advantages of being finer in focal point, free from any consuming component parts, being capable of freely controlling a powerful ultrasonic pressure as well as a focal point position by the phase control of a drive voltage on a plurality of piezoelements, and so on.

In the field of the cancer treatments, on the other hand, the MIT constitutes one of key words. For the cancers in particular, most of their medical treatments have currently been made by a surgical procedure and, in this case, their involved organs, etc. are greatly damaged, many times, in functions and external appearances and the patient, even if surviving such surgical operation, has to suffer a greater burden. For this reason, therefore, there is a strong desire that less invasive procedure be carried out while not affecting the QOL (quality of life).

In such a trend, recent focus has been on the hyperthermic treatment on the malignant neoplasm, that is, the cancer therapy. This is the therapy by which, through the utilization of the difference in heat sensitivity between the cancerous tissue and the normal tissue, only the cancerous cells are selectively killed by applying heat there and maintaining that area to about 42.5 to 43° C. A preceding method of heating is by using an electromagnetic wave, such as a microwave, but it is difficult for this method to selectively heat any deeply-seated tumors because it is due to the electrical property of the living body. And no better therapeutic outcome can be expected for those tumors present at a depth of over 5 cm. For this reason, it may be considered that, for the treatment on the deeply-seated tumors, use is made of an ultrasonic energy capable of reaching their sites with a better focus.

With such a hyperthermic treatment one step further it has also been considered that the tumor tissue is momentarily thermodegenerated and necrotized by heating, to over 80° C., a tumor site by a sharply focused, powerful ultrasonic wave generated from the piezoelements.

In this medical treatment, unlike the conventional hyperthermia, a very powerful (several hundreds to several thousands $W/cm^2$) ultrasonic wave is applied to a region restricted at and near its focal point and, therefore, only that region is instantly thermodegenerated/necrotized. And since it is necessary to cauterize the whole affected region while accurately positioning that focal point, a focal point positioning technique becomes of importance.

As one solution relating to this matter, a technique is disclosed by which a heat increasing area during an operation is measured by a temperature distribution imaging utilizing a chemical shift at an MRI.

Further, with regard to the system using an ultrasonic wave alone, a technique is disclosed by which an echo wave is detected from the focal spot area of a therapeutic ultrasonic wave and displayed on the ultrasonic image.

In the ultrasonic wave diagnosis apparatus of a type using a simple B-mode cross-sectional image, in particular, as an "in-operation" monitor, it is not possible to grasp the whole tumor region, at a time, by one image plane of the B-mode cross-sectional image. Even if, therefore, a given cauterizing area is set, there are sometimes the cases where it is shifted relative to an actual affected region in terms of its setting position and range. If, therefore, irradiation is made in spite of this, some area of the tumor is not shot with the ultrasonic wave and, moreover, there is a risk that its surrounding normal tissue will be wastefully injured.

In the conventional ultrasonic diagnostic apparatus, there is no practical means for previously checking, for example, "to what extent an incident path of the therapeutic ultrasonic wave overlaps with the surrounding organs" or "how safe it is to continue its irradiation", in a simple and real-time fashion and there is no way but to follow a pre-operative therapy plan. Under these situations, it has not been possible to make any corresponding correction against the actual movement of the organs and deviation in the incident path of the therapeutic ultrasonic wave. For this reason there is a risk that any important organ will unintentionally be adversely affected upon irradiation with the ultrasonic wave on its way and that, during the shifting of the ultrasonic wave, its applicator will be aimed at an area away from its originally intended site.

In the case where the diagnostic apparatus, such as MRI (magnetic resonance imaging) apparatus, is used, during the "in-operation" time, for an image monitoring purpose, it is possible to acquire three-dimensional image data and hence to make such control that any important organ is not unintentionally involved on a way of the therapeutic ultrasonic wave. However, this is simply based on an assumption and it is not possible to simply check "an adverse effect introduced on an intermediate way of any powerful ultrasonic wave from an actual shooting position", "a variation in a positional relation of the respiratory motion, etc., to the surrounding organs and its adverse effect", "any hindrance of the applicator by other sites when it has been moved to an actual shooting position", and so on.

BRIEF SUMMARY OF THE INVENTION

It is accordingly the object of the present invention to provide an ultrasonic wave diagnosis apparatus which can safely and positively irradiate a therapy ultrasonic wave.

When an affected region is greater than a focal point of a therapy ultrasonic wave, a therapy region is set in a way to include the affected region. The focal point of the therapy ultrasonic wave is moved along a planned course designed based on the therapy region, so that it is possible to treat that whole affected region greater than the focal point. In the present invention, before an actual therapy, that is, before irradiation with the therapy ultrasonic wave, a therapy simulation is made to see whether or not a better treatment is carried out. In the therapy simulation, an applicator is moved in accordance with a planned course designed based on the therapy region. During the movement, the internal region of a human subject is continuously scanned and imaged by the ultrasonic probe.

A cross-sectional image obtained is displayed together with a focal point marker representing the focal point. In this way, the applicator is moved along an actual planned course and, by observing a positional relation between the subject and the focal point, accurate checking is made to see whether or not the therapy region is set relative to the affected region.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 5A shows an explanatory view showing a method for adjusting the position of the cauterizing region at a step ST6 in FIG. 2;

FIG. 5B shows an explanation view showing a method for adjusting the size of the cauterizing region at a step ST6 in FIG. 2;

FIG. 6A is a view showing a method for effecting scanning in a simpler mode at a simulation step ST7 in FIG. 2;

FIG. 6B is a view showing a change of a cross-sectional image in accordance with a scanning method in FIG. 6A;

DETAILED DESCRIPTION OF THE INVENTION

Figure 1:
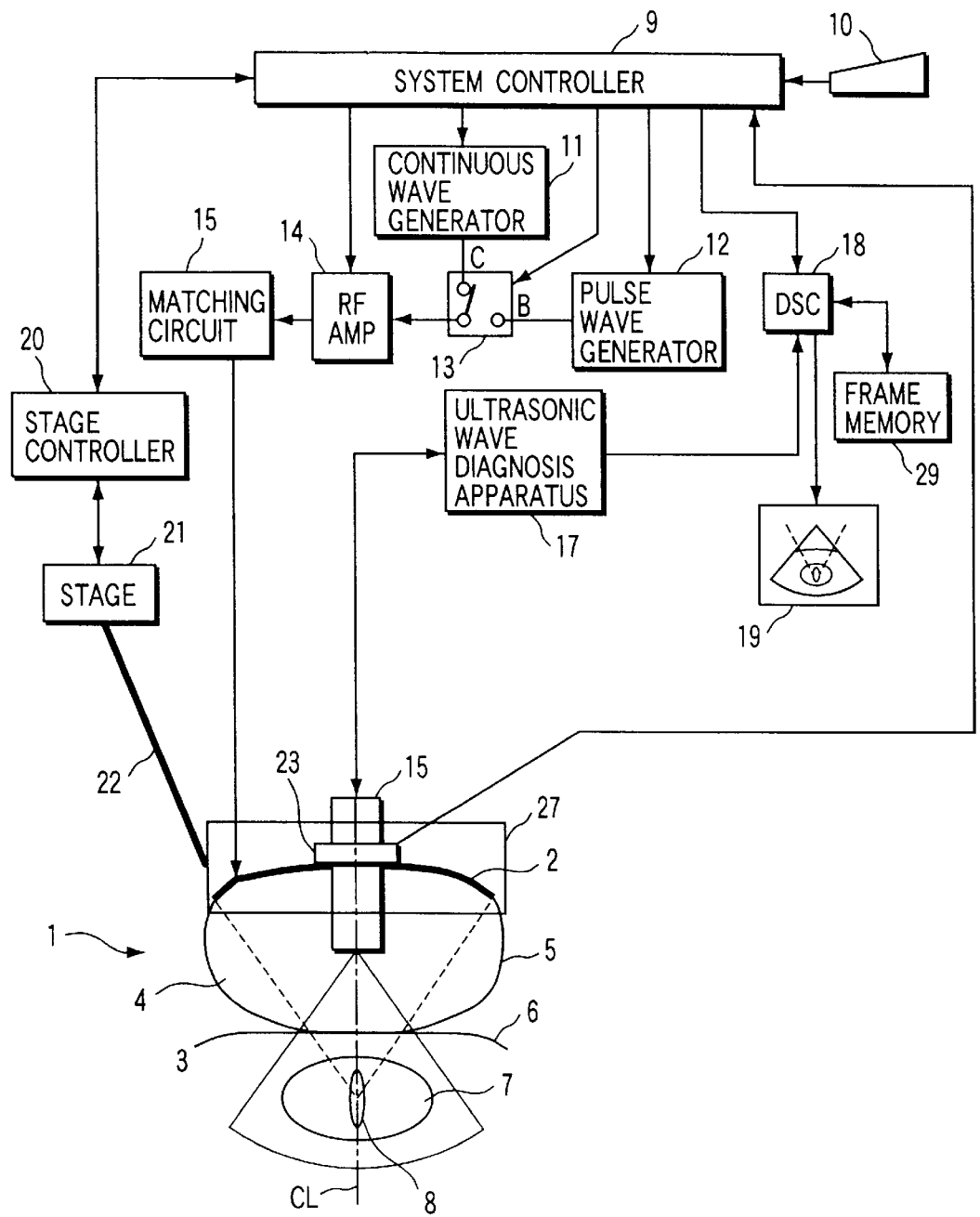
FIG. 1 is a block diagram showing an arrangement of an ultrasonic wave diagnosis apparatus according to a preferred embodiment of the present invention.

A preferred embodiment of the present invention will be given below with reference to the drawing.

FIG. 1 shows an arrangement of an ultrasonic wave diagnosis apparatus of the present embodiment. An applicator has a frame 27 with a therapy ultrasonic wave generation source 2 attached thereto. The ultrasonic wave generation source 2 has a piezoelement or piezoelement group formed as a part-circular section or as an array to generate a powerful ultrasonic wave. The therapy ultrasonic wave from the piezoelement is focused at a depth point, that is, a center of the part-circular section, on the center axis CL of the ultrasonic wave generation source 2. An area showing an energy exceeding a given level with this focal point as a center is generally referred to as a focal point 8. This focal point 8 has an elongated spot of, for example, a length of 15 mm in length and 10 mm in diameter.

The frame 27 and ultrasonic wave generation source 2 have a hole at their substantially central areas and a cylindrical type ultrasonic probe 16 is fitted in the hole such that it has its axis set on the center axis CL of the ultrasonic wave source 2 and is inserted in the hole to allow it to be axially moved in a front/back direction. An encoder 23 is so provided as to detect an amount of projection of the ultrasonic probe 16 relative to the ultrasonic wave generation source 2. Since the ultrasonic probe 16 is so provided relative to the ultrasonic wave generation source 2, the focal point 8 of the ultrasonic wave generation source 2 is present on its center line where a cross-sectional image is obtained by the ultrasonic probe 16 and the depth of the focal point can be calculated based on the projection amount detected by the encoder 23.

An ultrasonic wave diagnosis apparatus 17 is provided to allow the focal point 8 area to be scanned, with an ultrasonic wave, by means of the ultrasonic probe 16 and a corresponding cross-sectional image to be displayed on a CRT 19 through a digital scan converter (DSC) 18. Under control of a system controller 9 a focal point marker corresponding to the focal point, as well as a pattern marker representing a cauterizing region (a therapy region) set through a console panel 10, is superimposed on the cross-sectional image on the CRT 19.

A coupling film 5 is provided on the lower side of the ultrasonic wave generation source 2 and ultrasonic probe 16 and filled with a coupling solution 4, such as a deaerated water, so as to lead the therapy ultrasonic wave, as well as an ultrasonic wave for imaging, to a patient with less loss and an echo from the patient to the ultrasonic wave 16 with less loss.

The applicator 1 has its frame 27 mounted on a forward end of an arm 22 extending from a stage 21 and is freely movable with the stage 21 and can be stopped at a free posture. The movement of the arm 22 is completely controlled by means of a stage controller which is in turn controlled by a system controller 9.

At a time of diagnosis, first the patient lies on a bed, not shown, and is immobilized to a predetermined position. And the coupling film 5 of the applicator 1 is set in contact with the body surface of the patient, that is, the body surface locally coated with a jelly, not shown, for ultrasonic diagnosis. A high-frequency signal of an ultrasonic wave range is supplied from a continuous wave generator 12 or a pulse wave generator 12 through a changeover switch 12 in accordance with a control signal from the system controller 9. The high-frequency signal is amplified by a RF amplifier 14 and supplied past an impedance matching circuit 15 to the piezoelement of the therapy ultrasonic wave generation source 2. By doing so, the piezoelement is mechanically oscillated to produce an ultrasonic wave. The ultrasonic wave is guided past the coupling solution 4 into the patient body where its focal point 8 is created. An affected region (tumor or calculus) at the focal point 8 is treated (heated or crushed).

Figure 2:
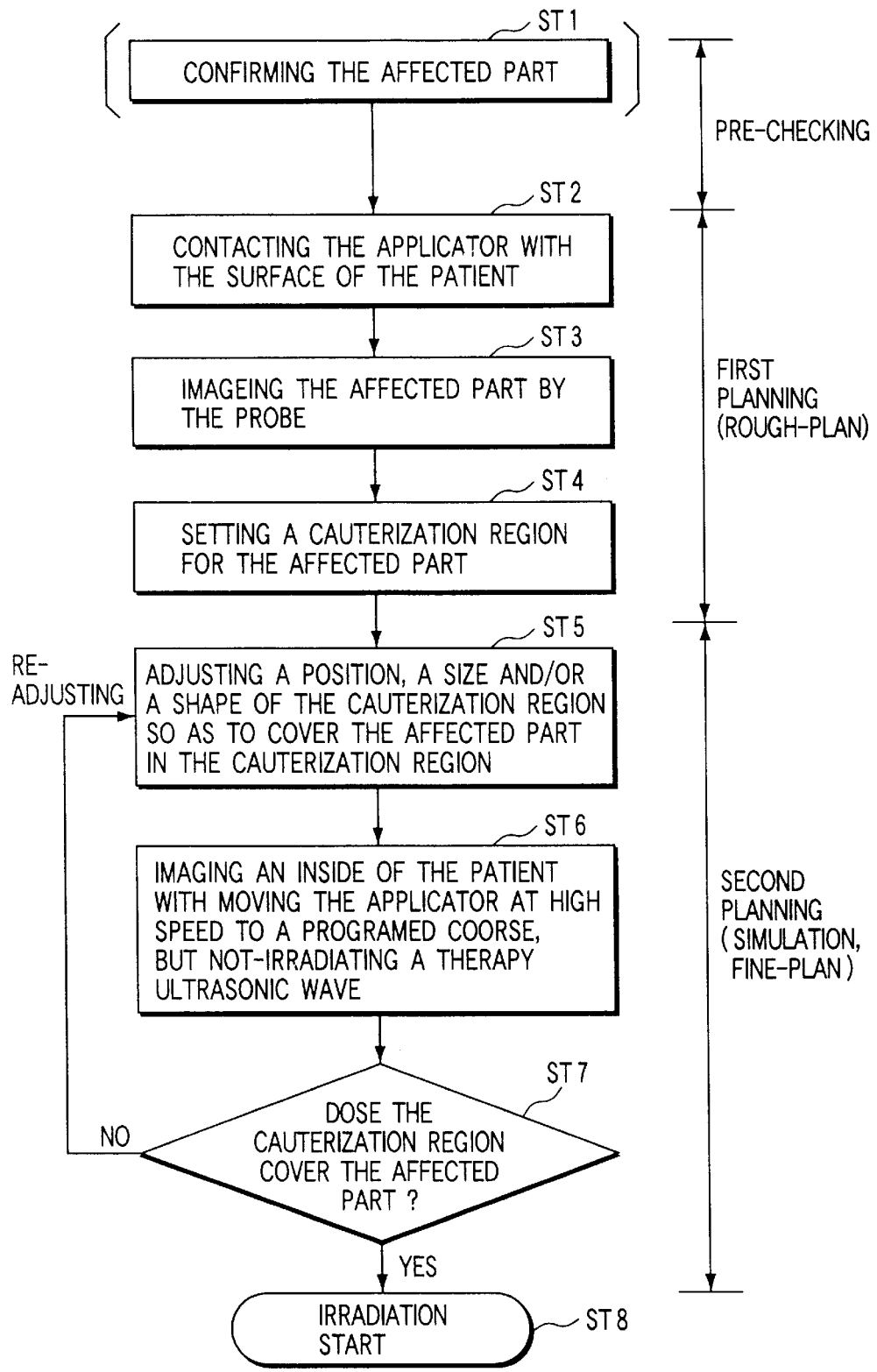
FIG. 2 is a flow chart showing a flow of a planned therapy done with the diagnosis apparatus.

FIG. 2 shows a planning procedure of diagnosis to be done on the present embodiment. Here, an explanation will be given below about cauterizing the tumor, such as a cancer, with an ultrasonic wave. In the case where an affected part 7 is greater than the focal point 8, it is necessary that the affected part 7 be treated by making a repeated irradiation with the ultrasonic wave while shifting the focal point 8. The shifting range of the focal point 8 is determined as a cauterizing region (therapy region). The greatest object of the present invention is to correctly set a cauterizing region on the affected part, that is, to cover the affected part with the cauterizing region to neither too deficient nor too excessive extent.

The planned procedure of diagnosis is broadly divided into a pre-checking, a first planning and a second planning stage. Of these, the second planning stage is characteristic of the present embodiment.

First, at a stage of confirming the affected part (ST1), the ultrasonic wave generator 2 is not driven and any therapy ultrasonic wave is not generated in which case the inside of the patient is scanned with an imaging ultrasonic wave to acquire a corresponding cross-sectional image and, by doing so, to observe the inside of the patient through the cross-sectional image. As the case may be, an X-ray CT image, MRI image, etc., are referred to and, by this pre-checking ST1, confirmation is made as to the general position, size and shape of the affected part (region) of the patient.

In the first planning stage, the cauterizing region is set roughly. The applicator 1 is set in contact with the body surface of the affected region confirmed at the pre-checking planning stage (ST2) and the affected region is imaged through the ultrasonic probe 16 in a three-dimensional way (ST3). And the cauterizing region is so set as to cover the affected region 7 (ST4).

Figure 4A:
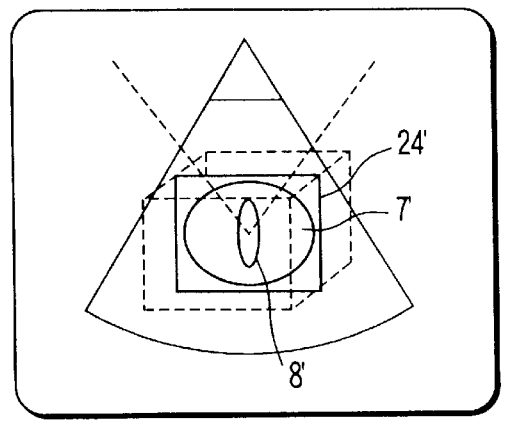
FIG. 4A is a view showing the screen images corresponding to the steps ST5 and ST6.

FIG. 4A shows a set image screen corresponding to the cauterizing region. On the image screen are displayed an affected region image 7', focal point marker 8' and cauterizing region marker 24'. The general procedure for setting the cauterizing region is as set out below. When the focal point marker 8' is located at the center of the affected image 7', the cauterizing region marker 24' is displayed, for example, as a rectangular configuration with the focal point marker 8' set at a center. And the position and size of the cauterizing region marker 24' are so adjusted as to cover the affected region image 7'. By repeating this operation while changing the position of the cross-sectional image, the cauterizing region is roughly set.

When the cauterizing region is so set, the moving course of the focal point 8 is designed along the set cauterizing region. The moving course may be designed by changing the size of a basic course, such as a rectangular waveform, spiral form, etc., or be freely designed in accordance with the cauterizing region.

Further, the focal point marker 8' may be displayed as a general shape and size or as a more accurate shape and size. In the latter case, reference is made to the intensity distribution of the therapy ultrasonic wave. For the intensity distribution image, the therapy ultrasonic wave pulse is actually generated from the source 2, the corresponding echo is received by the ultrasonic probe 16 and a B mode image is generated based on the received echo signal. For the B mode, the echo of a stronger intensity level is displayed with high luminance. Further, the echo intensity reflects the irradiation intensity at its position, so that the B mode image displays the intensity distribution of the therapy ultrasonic wave. From this intensity distribution it is possible to extract, as a focal point 8, the region where a level exceeding a given intensity is displayed. For the detail of the intensity distribution imaging, a description is given about the procedure of receiving/imaging, by a therapy ultrasonic probe, those high harmonic components of a burst wave irradiated from an ultrasonic wave generating source for generating a therapy strong ultrasonic wave as in JPN PAT NOS. 1851304 and 1821772, the color Doppler-applied procedure as in JPN PAT APPLN KOKOKU PUBLICATION NO. 7-203576, and the procedure of, without transmitting an image acquisition ultrasonic wave from a diagnostic ultrasonic wave probe, receiving only an ultrasonic wave irradiated from a therapy ultrasonic wave source and imaging an echo wave from a living tissue as in JPN PAT APPLN NO. 1765452.

Figure 3A:
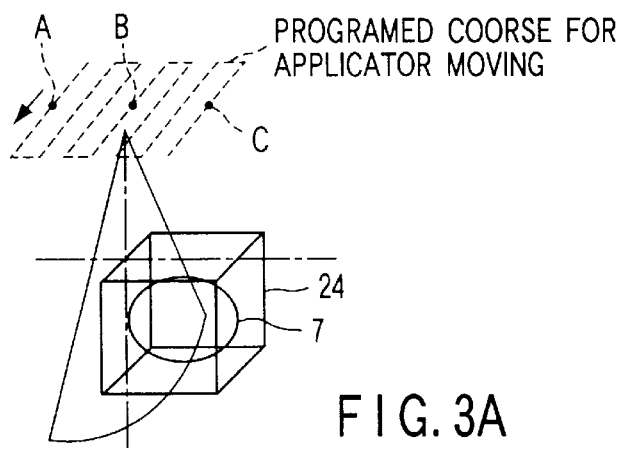
FIG. 3A is a view showing the movement of an applicator at a simulation step ST7 in FIG. 2.
Figure 3B:
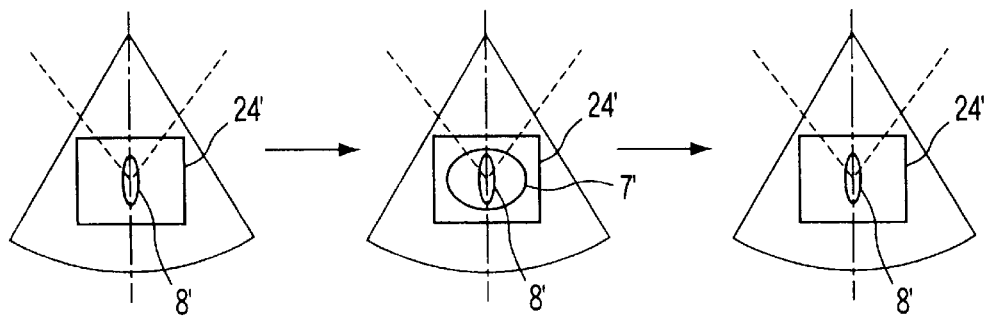
FIG. 3B is a view showing a change of a cross-sectional image involving the movement in FIG. 3A.

Then the second planning stage is carried out. In the second planning stage, as shown in FIG. 3A, the applicator 1 is actually moved, under the control of the system controller 9, in accordance with a programmed course designed at the second planning stage (ST6). At this time, the therapy ultrasonic wave generation source 2 is not driven, so that the therapy ultrasonic wave is not generated. During the time period in which the applicator 1 is moved along the planned course, imaging is continued at and near a focal region by the ultrasonic probe 16 and diagnosis apparatus 17 and it is possible to observe a constantly changing image as shown in FIG. 3B. Needless to say, the focal point marker and cauterizing region are displayed together with this cross-sectional image. Such an operation will be referred to as a "therapy simulation". By this therapy simulation it is possible to check whether or not the cauterizing region is correctly set to the affected region (ST7).

In the actual therapy, the applicator 1 is intermittently moved along the planned course and, in synchronism therewith, the therapy ultrasonic wave is irradiated briefly at a stopped time, but, according to the therapy simulation above, the applicator 1 is moved continuously, that is, not interruptedly, and is so done at a higher speed than at the actual therapy time. It is, therefore, possible to largely reduce a required time and complete such a simulation.

Figure 4B:
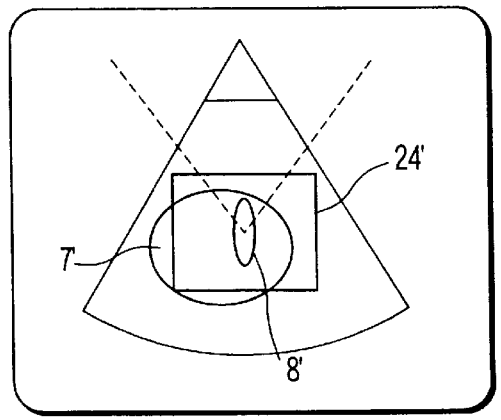
FIG. 4B is a view showing one form of a display image screen when a cauterizing region is deviated from an affected region.

If, as shown in FIG. 4B, the cauterizing region 24 is not correctly set to the affected region 7, the center position (coordinate) of the cauterizing region as well as its size and shape are finely adjusted (re-setted) through the console panel 10 (ST5). Changing the center position of the cauterizing region is achieved by dragging the cauterizing region marker 24' with the use of a pointing device such as a mouse as shown in FIG. 5A. Changing the size of the cauterizing region is achieved by dragging the cauterizing region marker 24', with the pointing device such as a mouse, and scaling it.

The therapy simulation ST6 is carried out after the re-setting of the cauterizing region and, by doing so, re-checking is made to see whether or not the cauterizing region 24 is correctly set relative to the affected region 7 (ST7).

The loop of the steps ST5, ST6 and ST7 is repeated until the cauterizing region 24 is correctly set to the affected region 7.

After the cauterizing region 24 is checked as being correctly set to the affected region 7, the affected region is actually irradiated with a therapy ultrasonic wave, thus starting a therapy step ST8. In the therapy, under the control of the system controller 9, the applicator 1 is moved along the planned course designed in accordance with the finally set cauterizing region. At this time, a switch SW13 is changed over to a C side and the ultrasonic wave generation source 2 is driven in accordance with a continuous high-frequency signal from the continuous wave generator 11, so that the therapy ultrasonic wave is continuously irradiated at the human subject.

According to the therapy simulation, checking is made to see whether or not the cauterizing region is correctly set and, by doing so, checking can be made for a brief period. In this case, fine control can be made as required. It is, therefore, possible to treat a region of interest in a safer, more positive and more highly reliable way. By actually moving the applicator 1 it is also possible to check whether or not the applicator 1 interferes with other objects, etc.

Figure 7:
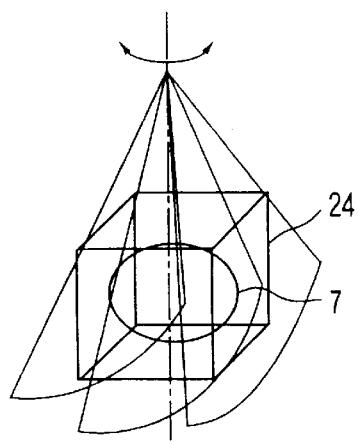
FIG. 7 shows another method for effecting scanning in a simpler mode.

An explanation will be given below about a simpler type simulation than the above-mentioned therapy simulation, that is, a simulation whereby it is possible to more simply check whether or not a cauterizing region is correctly set to an affected region. Although in the first-mentioned therapy simulation the applicator is moved in accordance with the actual planned course, the simpler type simulation adopts what is called a three-dimensional scanning method. As the three-dimensional type method use may be made of, for example, a method for rotating an ultrasonic probe 16 along an axis as shown in FIG. 6A, a method for swinging an ultrasonic probe 16 as shown in FIG. 7, and a method for linearly moving an ultrasonic probe 16. By observing a change of an image, as shown in FIG. 6B, obtained in a three-dimensional way it is possible to check whether or not a cauterizing region is correctly set to an affected region of a human being and to do this relatively accurately, for a brief way, in a three-dimensional way. This simpler type simulation may be used in combination with the above-mentioned therapy simulation.

Figure 8:
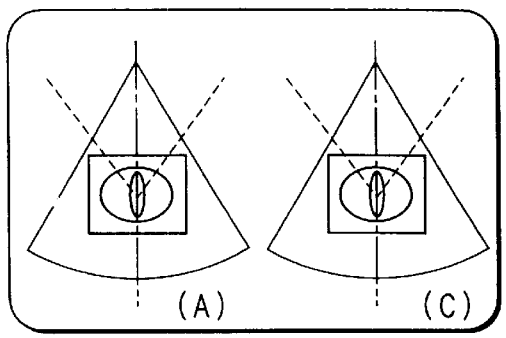
FIG. 8 is a view showing one form of a display image screen displaying images, corresponding to the ends of a cauterizing region, picked up from among those cross-sectional images in FIG. 3B.
Figure 9:
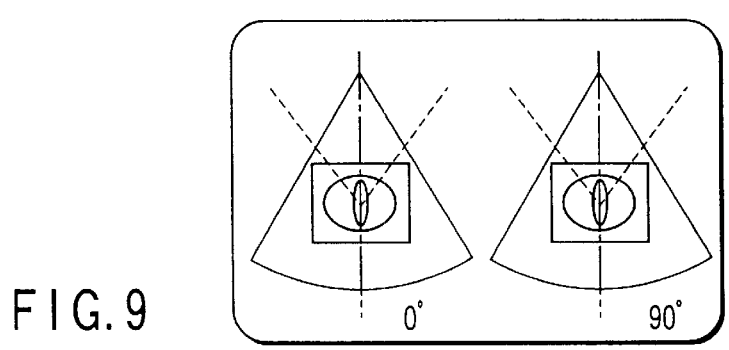
FIG. 9 is a view showing another form of a display image screen displaying images at 0° and 90° picked up from among those cross-sectional images in FIG. 6B.
Figure 10:
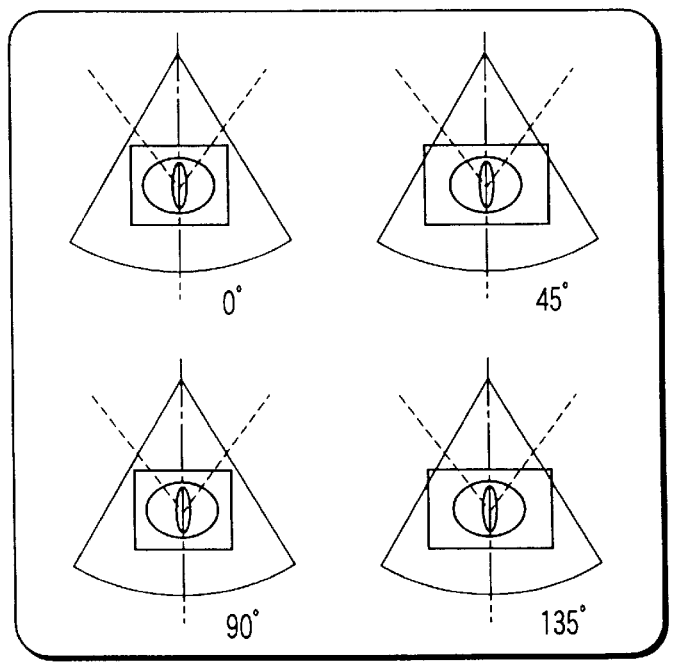
FIG. 10 is a view showing another form of a display image screen displaying images at 0°, 45°, 90°, 135° picked up from those cross-sectional images in FIG. 6B.

Then an explanation will be given below about a display method by which it is possible to easily check whether or not the cauterizing region is accurately set relative to the affected region. This display is automatically made by a system after the completion of the therapy simulation and simpler type simulation. A plurality of cross-sectional images are generated in the therapy simulation and simpler type simulation. A plurality of sheets of cross-sectional data are held in a frame memory 29. The system controller 9 enables some sheets of the cross-sectional images, that is, some sheets useful in making the above checking, to be picked up from those sheets of cross-sectional images and these useful sheets of the cross-sectional images to be displayed all at a time. As the useful sheets of the cross-sectional images there are those of two cross-sectional images obtained as desirable ones at two points A and C in FIG. 3A for instance, that is, those of cross-sectional images obtained by scanning the edges of the cauterizing region with the ultrasonic probe 16 (see FIG. 8). In the case where the ultrasonic probe 16 is rotated about the axis as shown in FIG. 6A, it is preferable that two sheets of cross-sectional images obtained, by scanning, at the two positions, 0° and 90°, for example, of the ultrasonic probe 16 be useful (see FIG. 9). It is also considered that, for example, four sheets of cross-sectional images obtained, by scanning, at four positions 0°, 45°, 90°, 135° of the ultrasonic probe 16 are displayed, as helpful cross-sectional images, all at a time (see FIG. 10).

Although the cross-sectional image has been explained as being displayed, it may be possible to prepare a three-dimensional image of an affected region from a plurality of sheets of cross-sectional image data and display it.

As the image acquisition means it is possible to use not only the ultrasonic probe but also an X-ray CT, MRI apparatus, etc. The pre-checking may be made while viewing not only the ultrasonic image but also other diagnostic images (2D, 3D) such as a simple X-ray image, X-ray CT image and MRI image.

Although, in the above-mentioned case, the applicator 1 is mechanically moved so as to shift the focal point, the present invention can be applied to the case where the focal point is electronically shifted with the use of a phased array type generation source and delay control method. Even in this case, under the therapy simulation, a scan plane is moved along a focal point shifting course.

Although the intensity distribution image is located on a center position of the cross-sectional image by controlling the generation timing of the therapy ultrasonic wave pulse for intensity distribution imaging and echo reception timing on the basis of an amount of extension of the ultrasonic probe 16 from the encoder 23, it may be possible to superimpose the intensity distribution image on a position corresponding to the amount of extension at the cross-sectional image. Further, although, in the above-mentioned case, the pulse wave generation circuit 12 is so provided as to be switchable to the continuous wave generator 11 for the intensity distribution imaging, it may be possible to provide the continuous wave generator 11 and emit a continuous wave for a relatively short time period only.

Although, in the present embodiment, the piezoelements are used as a strong ultrasonic wave generation source 2, an electromagnetic induction system for instance can be constructed so long as it can generate an ultrasonic wave as a continuous or near-continuous wave.

The present invention is not restricted to the above-mentioned embodiments and various changes or modifications can be made without departing from the spirit and scope of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed:

1. An ultrasonic therapy apparatus for focusing a therapy ultrasonic wave at an affected part for therapy, comprising:
   an applicator having a therapy ultrasonic wave generation source and ultrasonic probe;
   a mechanism for moving the applicator;
   a driver for driving the therapy ultrasonic wave generation source so as to generate the therapy ultrasonic wave from the therapy ultrasonic wave generation source;
   a diagnosis apparatus for driving the ultrasonic probe to scan a focal point and its neighborhood with the ultrasonic wave, forming a cross-sectional image based on an obtained echo and displaying the cross-sectional image;
   a console for setting a therapy region in a state to include the affected part; and
   a system controller for performing a therapy simulation, wherein,
   in the therapy simulation, the mechanism moves the applicator in accordance with a planned course of the focal point designed in a way to correspond to the therapy region, the driver does not drive the therapy ultrasonic wave generation source so that no therapy ultrasonic wave is generated, and the diagnosis apparatus scans the focal point and its neighborhood through the ultrasonic probe and displays, together with the cross-sectional image, a focal point marker representing the focal point.

2. The apparatus according to claim 1, wherein the console is provided for resetting at least one of a position, size and shape of the therapy region.

3. The apparatus according to claim 1, wherein the diagnosis apparatus is provided for displaying, together with the cross sectional image and focal point marker, a marker representing the therapy region.

4. The apparatus according to claim 1, wherein the diagnosis apparatus is provided for displaying an intensity distribution at and near the focal point of the therapy ultrasonic wave as the focal point marker.

5. The apparatus according to claim 1, wherein the diagnosis apparatus is provided for picking up a few cross-sectional images from among those cross-sectional images obtained during the therapy simulation and displaying the picked cross-sectional images all at a time on an image screen, the few images being obtained by scanning at and near the therapy region.

6. The apparatus according to claim 1, wherein the system controller enables a simpler type simulation to be performed and wherein, in the simpler type simulation, the driver does not drive the therapy ultrasonic wave generation source so that no therapy ultrasonic wave is generated and the diagnosis apparatus effects any of an axial rotation, swing and translation of the ultrasonic probe to generate a plurality of cross-sectional images and display these images.

7. The apparatus according to claim 6, wherein the diagnosis apparatus is provided for picking up a few cross-sectional images from among those cross-sectional images obtained during the simpler type simulation and displaying these cross-sectional images all at a time on an image screen, the few images being obtained by scanning at and near the therapy region.

8. The apparatus according to claim 6, wherein the diagnosis apparatus is provided for picking up two cross-sectional images from those cross-sectional images obtained from among the simpler type simulation and displaying these cross-sectional images all at a time on an image screen, the two cross-sectional images having their scan planes orthogonal to each other.

9. The apparatus according to claim 6, wherein the diagnosis apparatus is provided for picking up a plurality of cross-sectional images from among those cross-sectional images obtained during the simpler type simulation and displaying these cross-sectional images all at a time on an image screen, the cross-sectional images having their scan planes shifted at a predetermined angle with respect to each other.

10. An ultrasonic therapy apparatus for focusing a therapy ultrasonic wave at an affected region for therapy, comprising:

means for generating a therapy ultrasonic wave;

means for imaging a cross-sectional tissue associated with a focal point and its neighborhood of a therapy ultrasonic wave;

means for setting a therapy region including the affected region;

means for performing a therapy simulation, wherein, in a therapy simulation, no therapy ultrasonic wave is generated from the therapy ultrasonic wave generation source and a cross-sectional tissue is imaged and the imaged cross-sectional plane is moved in accordance with a planned course of the focal point of the therapy ultrasonic wave in a way to correspond to the therapy region.

11. The apparatus according to claim 10, wherein the setting means is provided for re-setting at least one of a position, size and shape of the therapy region.

12. The apparatus according to claim 10, wherein the imaging means is provided for displaying, together with the cross-sectional image, a focal point marker representing a focal point of the therapy ultrasonic wave.

13. The apparatus according to claim 12, wherein the imaging means is provided for displaying an intensity distribution at and near the focal point of the therapy ultrasonic wave as the focal point marker.

14. The apparatus according to claim 10, wherein the imaging means is provided for displaying, together with the cross-sectional image, a marker representing the therapy region.

15. The apparatus according to claim 10, wherein the imaging means is provided for picking up a few cross-sectional images from those cross-sectional images obtained in the therapy simulation and displaying these cross-sectional images all at a time on an image screen, the few cross-sectional images being obtained by scanning at and near the therapy region.

16. The apparatus according to claim 10, wherein the imaging means is provided for picking up two cross-sectional images from among those cross-sectional images obtained in the therapy simulation and displaying these cross-sectional images all at a time on an image screen, the two cross-sectional images having scan planes orthogonal to each other.

17. The apparatus according to claim 10, wherein the imaging means is provided for picking up a plurality of cross-sectional images from among those cross-sectional images obtained in the therapy simulation and displaying these cross-sectional images all at a time on an image screen, the cross-sectional images having scan planes shifted at a predetermined angle with respect to each other.

18. An ultrasonic therapy apparatus for focusing a therapy ultrasonic wave at an affected region for therapy, comprising:

means for generating a therapy ultrasonic wave;

means for imaging a cross-sectional tissue associated with a focal point and its neighborhood of the therapy ultrasonic wave;

means for setting a therapy region including the affected region; and means for performing a therapy simulation, wherein, in the therapy simulation, no therapy ultrasonic wave is generated from the therapy ultrasonic wave generation source, the therapy region is scanned by effecting an axial rotation, swing and translation with the ultrasonic wave, the cross-sectional image associated with the cross-sectional tissue is displayed and the cross-sectional image is displayed together with a marker representing the focal point and marker representing the therapy region.

19. A method for planning before treating an affected region of a subject while moving a focal point of a therapy ultrasonic wave relative to the affected region, comprising the steps of:

(a) setting a therapy region in a way to correspond to the affected region;

(b) simulating the therapy after the first step; and
(c) re-setting the therapy region in accordance with a result of the therapy simulation;

wherein, in the second step (b), no therapy ultrasonic wave is generated, a cross-sectional tissue is imaged and an imaged cross-sectional plane is moved in accordance with a planned course of the focal point designed based on the set therapy region.

* * * * *